United States Patent
Huang

(10) Patent No.: US 7,964,704 B2
(45) Date of Patent: Jun. 21, 2011

(54) PREPARATION OF HIGH PURITY COLLAGEN

(75) Inventor: Lynn L. H. Huang, Yongkang (TW)

(73) Assignees: Life Fusion, LLC, Fremont, CA (US); National Cheng Kung University, Tainan, Taiwan (CN)

( * ) Notice: Subject to any disclaimer, the term of this patent is extended or adjusted under 35 U.S.C. 154(b) by 86 days.

(21) Appl. No.: 12/509,759

(22) Filed: Jul. 27, 2009

(65) Prior Publication Data

US 2011/0020864 A1 Jan. 27, 2011

(51) Int. Cl.
*C09H 1/00* (2006.01)
*C07K 1/00* (2006.01)
(52) U.S. Cl. .................................. 530/356; 530/412

(58) Field of Classification Search ................. None
See application file for complete search history.

(56) References Cited

U.S. PATENT DOCUMENTS

| | | |
|---|---|---|
| 3,368,911 A | 2/1968 | Kuntz et al. |
| 4,185,011 A | 1/1980 | Berg et al. |
| 4,320,201 A | 3/1982 | Berg et al. |
| 4,837,285 A | 6/1989 | Berg et al. |
| 5,210,182 A | 5/1993 | Nasrallah et al. |
| 5,374,539 A | 12/1994 | Nimni et al. |
| 5,436,135 A | 7/1995 | Tayot et al. |
| 5,993,844 A | 11/1999 | Abraham et al. |
| 7,498,412 B2 | 3/2009 | Huang et al. |
| 2003/0004315 A1 | 1/2003 | Macdonald et al. |
| 2008/0268052 A1 | 10/2008 | Voytik-Harbin et al. |

*Primary Examiner* — Suzanne M. Noakes
(74) *Attorney, Agent, or Firm* — Frenkel & Associates

(57) ABSTRACT

A method of preparing collagen by first producing a collagen matrix and then extracting collagen from the matrix.

21 Claims, No Drawings

PREPARATION OF HIGH PURITY COLLAGEN

BACKGROUND OF THE INVENTION

Collagen is a fibrous protein, which can be found in cartilage, tendon, dermis, and other connective tissues. It has been widely used in both industry and medicine.

Typically, collagen is isolated from connective tissues by acidic or enzymatic treatment that removes non-collagenous material. To improve collagen purity, this treatment must be repeated several times. The repetitive treatment not only prolongs the isolation process but also results in low collagen yields.

There is a need for a new method of preparing high purity collagen.

SUMMARY OF THE INVENTION

The present invention features a method for preparing high purity collagen by first producing a collagen matrix from a connective tissue (e.g., dermis or tendon) and then extracting collagen from the matrix. More specifically, this method includes the following steps: (i) providing a connective tissue having a surface ranging from 20 $mm^2$ to 2 $m^2$ (e.g., 25 $mm^2$ to 900 $cm^2$), (ii) swelling the connective tissue with a first acidic solution by at least 50% (e.g., 100% to 500%) in volume to form a swollen connective tissue, (iii) washing the swollen connective tissue to remove non-collagenous material, thereby forming a collagen matrix, and (iv) extracting collagen from the collagen matrix with an extraction solution to produce a collagen-containing solution.

The swelling step can be performed by soaking the connective tissue in the first acidic solution. Preferably, the soaking process is performed concurrently by squirting a liquid into the connective tissue or by ultrasound treatment. The first acidic solution has a pH of 1-6 (e.g., 2-4) and is substantially free of salt, i.e., having no salt or having salt at a very low concentration so that the ionic strength of the solution is not greater than 0.005 M. This acidic solution can be prepared from, among others, formic acid, oxalic acid, acetic acid, citric acid, lactic acid, malic acid, boric acid, phosphoric acid, or a mixture thereof. Preferably, it is a 0.1-6 M acetic acid solution.

After the swelling step, the resultant swollen connective tissue can be washed to remove non-collagen material, thereby producing a collagen matrix. The washing step can be performed by soaking the swollen connective tissue in a wash solution containing a detergent, a proteolytic enzyme, or a mixture thereof, during the soaking process, the swollen connective tissue can be subjected to ultrasound treatment or liquid-squirting treatment.

The collagen matrix is then soaked in an extraction solution to form a collagen-containing solution. The extraction solution can be an acidic solution containing a weak organic acid, e.g., oxalic acid, acetic acid, citric acid, lactic acid, malic acid, boric acid, phosphoric acid, or a mixture thereof, at a pH suitable for collagen dissolution (e.g., lower than 4). Alternatively, the extraction solution is a neutral solution (e.g., 0.05 M Tris buffer) containing a salt (e.g., NaCl or KCl) at a concentration suitable for collagen dissolution (e.g., 1M). In one example, collagen is extracted from the collagen matrix by comminuting the collagen matrix to produce collagen powders and mixing the powders with an extraction solution to produce a collagen-containing solution. The comminuting and mixing steps can be conducted simultaneously.

The collagen can subsequently be precipitated from the collagen-containing solution by conventional methods. In one example, the collagen is precipitated by dialysis. In another example, it is precipitated by mixing the solution with a salt to a concentration of 1.0-4.0 M. The collagen thus obtained is preferably desalted. In yet another example, the collagen is precipitated by adjusting the pH of the collagen-containing solution to 4.5-8.

The collagen thus prepared can be freeze-dried, air-dried, or vacuum-dried to form collagen powders, sponges, sheets, or membranes. Collagen powders thus prepared can be dispersed in an acidic solution to form a collagen dispersion, or treated with a proteolytic enzyme to produce atelopeptide collagen. Examples of the proteolytic enzyme include, but are not limited to, pepsin, bromelain, chymopapain, chymotrypsin, collagenase, ficin, papain, peptidase, proteinase A, proteinase K, trypsin, microbial proteases, and a mixture thereof.

The details of one or more embodiments of the invention are set forth in the description below. Other features or advantages of the present invention will be apparent from the following detailed description of several examples, and also from the appended claims.

DETAILED DESCRIPTION OF THE INVENTION

Collagen is a triple-helix, rod-shaped molecule having a length of about 300 nm and a diameter of about 1.5 nm. A number of collagen molecules form a collagen fibril and a bundle of collagen fibrils form a collagen fiber. Covalent cross-linking exists inter- and intra-collagen molecules, thereby forming a fibrous network in a connective tissue.

Described herein is a method for preparing high purity collagen by first producing a porous collagen matrix directly from a connective tissue and then extracting collagen from the collagen matrix.

Preparation of Collagen Matrix

The starting material, i.e., a connective tissue, can be derived from an animal, e.g., cattle, pigs, horses, sheep, chickens, ducks, turkeys, gooses, whales, and sharks. Connective tissues suitable for making the collagen matrix include, but are not limited to, dermis, subcutaneous tissue, ligament, tendon, aponeurose, cartilage, and bone tissue. If necessary, a connective tissue is first cleaned manually (e.g., by gross dissection) or mechanically to remove undesirable materials such as fat and lipid. In one example, a dermis is obtained by removing lipid from a fresh animal skin, washing the skin with saline several times, and removing the surface layer of the animal skin with a dermatome to obtain the dermis. The dermis can be further washed with a phosphate buffered saline solution.

If desired, a connective tissue can be first treated with a suitable organic solvent or a mixture of the organic solvent and water to allow penetration of the organic solvent into the connective tissue. Examples of the organic solvents include, but not limited to, alcohol, ketone, acetone, acetonitrile, chloroform, N,N-dimethylformamide, dimethyl sulfoxide, or a mixture thereof. When a mixture of an organic solvent and water is used, the ratio between the organic solvent and water is above 1:5 (e.g., 1:4, 1:1, or 4:1).

When a connective tissue contains hairs or hair roots, it can be treated with a proteolytic enzyme (e.g., dispase, trypsin, papain, pepsin, chymotrypsin, bromelain, ficin, or a mixture thereof) that breaks down the hairs or hair roots.

Any of the connective tissues described above is then soaked in an effective amount of an acidic solution for a sufficient period to allow swelling of the connective tissue to a desired level, i.e., having a thickness of at least about 50% greater than (e.g., 2-5 times of) the original thickness. The acidic solution can be prepared from an organic acid, e.g., formic acid, oxalic acid, acetic acid, citric acid, lactic acid, malic acid, boric acid, phosphoric acid, or mixtures thereof. In one example, the acidic solution is an acetic acid solution having a concentration of 0.1 to 6 M (e.g., 0.1-2 M or 0.5 to 1.25M). To achieve a better swelling effect, the acidic solution used in the present invention is substantially free of salt.

In the swelling step, the connective tissue is suspended in the acidic solution described above. If desired, a stream of liquid or a plurality of liquid streams can be applied to the connective tissue to facilitate penetration of the acidic solution into the tissue and reducing the time needed for swelling the connective tissue to a desired level. The liquid streams can be jetted out from a nozzle or an orifice installed in a container, where the connective tissue and the acidic solution are placed.

Alternatively or in addition, an ultrasonic wave (generated by, e.g., a supersonic vibration device) or a high frequency water wave (generated by e.g., an electromagnetic field) can be applied to the connective tissue soaked in the acidic solution to help penetration of the acidic solution into the connective tissue.

The swollen connective tissue obtained from the swelling step described above is washed using a wash solution to remove substantially the non-collagenous material from the swollen connective tissue, thereby producing a collagen matrix. The wash solution can contain a detergent, a chelating agent, a proteolytic enzyme, or a mixture thereof.

Exemplary detergents for preparing the wash solution include, but are not limited to, sodium dodecyl sulphate (SDS), Tego compounds (e.g., Tween 80, Triton W. R. 1339, p-isooctylpolyoxy-ethylene phenol polymer, and Triton A20), cetylpyridinium chloride, cetyltrimethyl-ammonium bromide, dioctyl sodium sulphosuccinate, Emasol 4130 (polyoxyethylene sorbitan monoleate), Lubrol W, Nonidet P40. In one example, a wash solution containing 0.01 to 10% of SDS is used to treat the swollen connective tissue at 4 to 45° C. for 1 to 150 hours.

Chelating agents contained in the wash solution include, but are not limited to, ethylene diamine tetra-acetic acid (EDTA), 1,4,7,10-tetraazacyclododecan-e-1,4,7,10-tetraacetic acid (DOTA), 1,4,7,10-tetraazacyclododecane-1,4,7,1-0-tetrakis(methylene phosphonic acid) (DOTP), trans-1,2-diaminocyclohexant-etra-acetic acid (CDTA), 4,5-dihydroxybenzene-1,3-disulphonic acid (Tiron), thiourea, 8-hydroxyquinoline-5-sulphonic acid, 3,6-disulpho-1,8-dihydroxy-naphthalene, Eriochromeschwarz T (1-(1-hydroxy-2-naphthylazo)-2-hydroxy-5-nitro-4-naphthalene sulphonic acid), ammonium purpurate, etc. Preferably, the chelating agent is EDTA at a concentration of 0.01 to 100 mM.

Alternatively or in addition, the wash solution can contain one or more proteolytic enzyme, e.g., ficin, pepsin, trypsin, dispase, and hermolysin for removing extracellular matrix associated proteins, other non-collagenous proteins and telopeptide of collagen molecules. Conditions used in a limited enzyme digestion, i.e., degrading non-collagen proteins while maintaining the integrity of collagen fibers, are well known in the art.

In the washing step, the swollen connective tissue can be suspended in any of the wash solutions mentioned above for a sufficient time. In one example, a stream of liquid or a plurality of liquid streams are jetted out from a nozzle or an orifice towards the swollen tissue to facilitate removal of non-collagenous materials. The liquid stream can be a stream of water, a detergent-containing solution, or an enzyme-containing solution. In another example, the swollen tissue, soaked in the wash solution, is treated by ultrasound to improve wash efficiency.

Conventional methods for removing non-collagenous material from connective tissues (see, e.g., U.S. Pat. Nos. 7,498,412, 5,993,844 and 5,374,539) can also be used in this invention.

The collagen matrix obtained from the washing step can be frozen in liquid nitrogen and then lyophilized for preservation. Alternatively, it can be soaked in a phosphate buffered saline solution and stored at 4° C. When necessary, the collagen matrix can be crosslinked by standard chemical or physical methods. Agents for cross-linking collagen molecules include glutaraldehyde, formaldehyde, carbodiimides, and certain polyepoxy compounds (e.g., glycol diglycidyl ether, polyol polyglycidyl ether and dicarboxylic acid diglycidylester).

The above-described method for preparing collagen matrices differs from the conventional methods in at least two aspects. First, it does not require rigorous physical or chemical treatment (e.g., grinding, homogenization, or harsh acidic/basic treatment) that disrupts the fibrous collagen network in connective tissues. Second, it uses an acidic solution substantially free of salt to swell a connective tissue, while salt is commonly used in the conventional methods for stabilizing collagen fibers.

Collagen Extraction from Collagen Matrix

A collagen matrix prepared by the above-described method can be comminuted by, e.g., agitation, stirring, homogenizing, mincing, tearing, cutting, grinding, shearing, or a mixture thereof. The collagen matrix, either intact or comminuted, can be soaked in an extraction solution for a suitable period to allow dissolution of collagen to a great extent. In one example, the comminuted collagen matrix is mixed with the extraction solution under gentle mechanical action (e.g., agitation, stirring, or blending) so as to facilitate collagen dissolution.

The extraction solution is an acidic solution or a neutral solution containing salt. It has a pH value or salt concentration at which collagen dissolves. Acids suitable for making the extraction solution include, but are not limited to, formic acid, oxalic acid, acetic acid, citric acid, lactic acid, malic acid, boric acid, phosphoric acid, and mixtures thereof. When acetic acid is used, its concentration can range from 0.1 to 6 M (e.g., 0.1-2 M or 0.5-1.25 M). Exemplary salts include KCl and NaCl and their concentration can range from 0.1 to 2 M (e.g., 1 M). Examples of neutral solutions include sodium phosphate buffer solution (PBS) and Tris buffer. When a neutral buffer solution having a pH of 7-8 is used, one or more neutral salts (e.g., 1M KCl or NaCl) can be added to the buffer solution to increase solubility of collagen in the buffer solution. Other buffer solutions suitable for making the extraction solution include, but are not limited to, glycine-HCl buffer, Clark and Lubs buffer, citric acid-$Na_2HPO_4$ buffer, Britton-Robinson buffer, citric acid-sodium citrate buffer, beta:beta'-dimethylglutaric acid-NaOH buffer, sodium acetate-sodium citrate buffer, succinic acid-NaOH buffer, sodium cacodylate-HCl buffer, sodium hydrogen maleate-NaOH buffer, $Na_2HPO_4$—$NaH_2PO_4$ buffer, sodium bicarbonate-5% $CO_2$ buffer, imidazole (glyoxaline)-HCl buffer, 2,4,6-trimethylpyridine (collidine) buffer, triethanolamine hydrochloride-NaOH buffer, sodium 5,5'-diethyl barbiturate buffer, dimethylleucylglycine buffer, and N-ethylmorpholine-HCl buffer.

After extraction, insoluble materials can be removed via, e.g., centrifugation or filtration, to produce a collagen-containing solution. If necessary, the insoluble materials can be extracted with the same extraction solution one or more times and the soluble fraction(s) can be combined with the collagen-containing solution.

The collagen-containing solution can be subjected to proteolytic enzyme digestion to remove telopeptides, thereby producing atelopeptide collagen. Proteolytic enzymes suitable for this digestion include, but are not limited to, pepsin, bromelain, chymopapain, chymotrypsin, collagenase, ficin, papain, peptidase, proteinase A, proteinase K, trypsin, microbial proteases, and mixtures thereof. Conditions for the digestion reaction vary, depending on the particular enzyme used. For example, when pepsin is used, the reaction mixture can have a pH about 2 to 5 and the concentration of the enzyme can be about 0.001 to 10 wt % of the collagen to be treated, which can have a concentration of 0.5 g/l to 10 g/l (e.g., 1 g/l to 5 g/l).

For further purification, the collagen can be precipitated from the collagen-containing solution mentioned above. This precipitation process can be repeated until achieving the desired purity level. In one example, the collagen is precipitated by dialyzing the collagen-containing solution against a buffered solution with a dialysis tubing having a molecular weight cut-off about 12,000 to about 14,000. In another example, the collagen is precipitated by adding a salt (e.g., an alkali metal halide, such as NaCl) to the collagen-containing solution to a concentration of about 1.0 M to 4.0 M, collected by centrifugation, and then desalted by ultrafiltration, dialysis or washing with a dilute acid solution. In still another example, the collagen is precipitated by adjusting the pH of the collagen-containing solution to a pH value at which collagen is insoluble. See WO/2004/096834. Collagen purification can also be achieved by a combination of any of the methods described above. The collagen thus precipitated can be re-suspended and subjected to a buffer exchange using an ultrafiltration membrane.

The collagen obtained from any of the methods described above can be lyophilized under a vacuum. Alternatively, it can be re-suspended in a suitable solution.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All publications cited herein are incorporated by reference.

Example 1

Preparing Collagen Matrices

The skin of a pig was harvested. After removal of lipids, the skin was washed a few times with saline. The surface layer of the skin was removed with a dermatome to obtain the dermis having a thickness of 0.3 mm. The dermis was further washed with a phosphate buffered saline. After washing, any saline residue was completely removed from the surface of the dermis.

The dermis was placed in a container filled with 0.5 M acetic acid and incubated at 37° C. for one and half days to allow swelling of the dermis to a thickness of 0.45 mm. During incubation, the container was placed on a shaker to allow suspension of the dermis.

The swollen dermis thus produced was then soaked in a solution containing SDS (0.5%) and EDTA (0.5 mM) or 2 hours at room temperature to remove non-collagenous material and produce a collagen matrix. The collagen matrix was washed with an aseptic phosphate buffered saline solution to remove the residual SDS and EDTA.

Example 2

Extracting Collagen from Collagen Matrices

The collagen matrices prepared by the method described in Example 1 above were soaked in a 0.5 M acetic acid solution for 12-24 hours with stirring. The resulting mixture was centrifuged at 2000 rpm (700×g) for 1 hour and the supernatant was collected and stored at 4° C.

The supernatant containing the isolated collagen was treated with pepsin (0.2 mg/ml) for 24 hours to produce atelopeptide collagen.

Example 3

Collagen Purification via Dialysis

Collagen was extracted from the collagen matrices prepared by the method described in Example 2 above to produce a collagen-containing solution. The solution was dialyzed against a 0.02 M disodium hydrogen phosphate buffer with a cellulose dialysis membrane (MWCO 12-14,000) and subsequently centrifuged at 8000×g for 1 hour. The pellet was collected, rinsed with cold MilliQ water several times, and then re-suspended in cold MilliQ water. The suspension was centrifuged at 8000×g for 1 hour.

The resulting collagen pellet was resuspended in 0.1M acetic acid.

Example 4

Collagen Purification via Salting-Out or pH Change

Collagen was extracted from the collagen matrices following the method described in Example 2 above, resulting in a collagen-containing solution.

Sodium chloride was added to the solution gradually to a final concentration of 2.5 M. The collagen precipitated in this process was collected, washed with distilled water, and then resuspended in a 0.1M acetic acid solution.

Alternatively, 1 M NaOH was added to the collagen-containing solution to adjust its pH to 7. The mixture was kept in a cold room with constant stirring for 3 hours to allow collagen precipitation. Afterwards, the mixture was centrifuged at 4° C. for 10 minutes and the collagen pellet was resuspended in de-ionized water. The pH of the suspension was adjusted to below 3.5 with 0.1M HCl to allow collagen dissolution.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. A method for producing a collagen preparation, comprising in the following order:
providing a connective tissue having a surface ranging from 20 mm$^2$ to 2 m$^2$,
swelling the connective tissue with a first acidic solution by at least 50% in volume to form a swollen connective tissue, wherein the acidic solution is substantially free of salt and has a pH of 1-6,
washing the swollen connective tissue to remove non-collagenous material in a wash solution comprising a detergent, chelating agent, protelyotyic enzyme or mixtures thereof, thereby producing a collagen matrix, and
extracting collagen from the collagen matrix with an extraction solution to produce a collagen-containing solution.

2. The method according to claim 1, wherein the extracting step is performed by comminuting the collagen matrix to produce collagen powders and mixing the powders with the extraction solution to produce the collagen-containing solution.

3. The method according to claim 2, wherein the comminuting step and the mixing step are conducted simultaneously.

4. The method according to claim 1, further comprising, after the extracting step, precipitating the collagen from the collagen-containing solution and drying the collagen or dispersing the collagen in a second acidic solution.

5. The method of claim 4, wherein in the precipitating step, the collagen is precipitated by dialysis.

6. The method according to claim 4, wherein the precipitating step is performed by mixing the collagen-containing solution with a salt at a concentration of 1.0 M to 4.0 M to precipitate the collagen and the method further comprising, after the precipitating step, desalting the collagen.

7. The method according to claim 4, wherein the precipitating step is performed by adjusting the pH of the collagen-containing solution to 4.5-8 to precipitate the collagen.

8. The method according to claim 1, further comprising, after the extracting step, mixing the collagen-containing solution with a solution containing a proteolytic enzyme to produce a telopeptide collagen.

9. The method according to claim 8, wherein the proteolytic enzyme is selected from the group consisting of pepsin, bromelain, chymopapain, chymotrypsin, collagenase, ficin, papain, peptidase, proteinase A, proteinase K, trypsin, microbial proteases, and a mixture thereof.

10. The method according to claim 1, wherein the extraction solution contains an acid selected from the group consisting of formic acid, oxalic acid, acetic acid, citric acid, lactic acid, malic acid, boric acid, phosphoric acid, and a mixture thereof.

11. The method according to claim 1, wherein the extraction solution contains a salt.

12. The method according to claim 4, wherein the second acidic solution contains an acid selected from the group consisting of oxalic acid, acetic acid, citric acid, lactic acid, malic acid, boric acid, phosphoric acid, and a mixture thereof.

13. The method according to claim 1, wherein the swelling step is performed by soaking the connective tissue in the first acidic solution and concurrently squirting a liquid into the connective tissue.

14. The method according to claim 1, wherein the washing step is performed by soaking the swollen connective tissue in the wash solution and concurrently squirting a liquid into the swollen connective tissue.

15. The method according to claim 1, wherein the swelling step is performed by soaking the connective tissue in the first acidic solution and concurrently treating the connective tissue with ultrasound.

16. The method according to claim 1, wherein the washing step is performed by soaking the swollen connective tissue in the wash solution and concurrently treating the swollen connective tissue with ultrasound.

17. The method according to claim 1, wherein the connective tissue is derived from dermis or tendon.

18. The method according to claim 1, wherein the connective tissue has a surface ranging from 25 mm$^2$ to 900 cm$^2$.

19. The method according to claim 1, wherein the first acidic solution contains an acid selected from the group consisting of formic acid, oxalic acid, acetic acid, citric acid, lactic acid, malic acid, boric acid, phosphoric acid, and a mixture thereof.

20. The method according to claim 19, wherein the acidic solution has a pH value of 2 to 4.

21. The method according to claim 1, wherein the first acidic solution contains acetic acid at a concentration of 0.1-6 M.

* * * * *